United States Patent
Cussac et al.

[11] Patent Number: 5,195,379
[45] Date of Patent: Mar. 23, 1993

[54] TEST DEVICE FOR TRACTION AND COMPRESSION ON A TEST PIECE AFTER ATMOSPHERE RE-ENTRY SIMULATION

[75] Inventors: Michel Cussac, La Teste; Jean-Michel Lequertier, St. Aubin-de-Medoc, both of France

[73] Assignee: Aerospatiale - Societe Nationale Industrielle, Paris, France

[21] Appl. No.: 762,763

[22] Filed: Sep. 18, 1991

[30] Foreign Application Priority Data

Sep. 20, 1990 [FR] France ................................ 90 11602

[51] Int. Cl.$^5$ .............................................. G01N 3/02
[52] U.S. Cl. ........................................................ 73/859
[58] Field of Search ................... 73/859, 856, 857, 858, 73/860, 831, 833

[56] References Cited

U.S. PATENT DOCUMENTS

| 1,527,409 | 2/1925 | Hassel ........................ 73/859 |
| 2,537,322 | 1/1951 | Wanzenberg ................ 73/859 |

*Primary Examiner*—Jerry W. Myracle
*Attorney, Agent, or Firm*—Nikaido, Marmelstein, Murray & Oram

[57] ABSTRACT

A test piece subjected to a test is embodied from a pellet in which two half-moon shaped notches are embodied, the test piece taking support on two arc-shaped shoulders situated at the base of a clamping jaw extremity having a ribbed support plate. Two jaw extremities are disposed into a female clamping jaw of the test equipment. The present invention provides elements for measuring the residual resistance of a test piece following an atmospheric re-entry.

9 Claims, 3 Drawing Sheets

TEST DEVICE FOR TRACTION AND COMPRESSION ON A TEST PIECE AFTER ATMOSPHERE RE-ENTRY SIMULATION

FIELD OF THE INVENTION

The invention concerns a traction and compression test device intended in particular for measuring the residual stresses of a test piece having re-entered the atmosphere.

BACKGROUND OF THE INVENTION

A material having undergone re-entry or a simulated atmospheric re-entry may have undergone certain degradations modifying its resistance and accordingly it is important to be able to determine a residual rupture stress representative of the degraded state of said material.

Up until now, atmospheric re-entry simulations mainly form the subject of two types of analyses, namely visual appearance control and weight loss analysis. However, these analyses appear to be insufficient or inaccurate and it thus seems essential to obtain additional information making it possible to more reliably quantify this residual stress.

To obtain this information, traction tests are conducted on a test piece embodied from a pellet in which on each side half-moon shaped notches are embodied, thus facilitating sampling for a traction test. As these traction tests provide insufficient results, the Applicant has considered completing these tests by conducting compression tests and to this effect making use of a suitable device and tooling.

SUMMARY OF THE INVENTION

The object of the invention is to provide a traction and compression device used on a test piece after an atmospheric re-entry simulation using the self-closing traction clamping jaws of a test piece subjected to a test and obtained from a pellet in which two half-moon shaped notches have been embodied, this device being characterized in that tooling equipment connected to the jaws by self-closing means is adjusted to the arcs of a circle of the extremities of the test piece and is equally able to be used in traction and compression tests.

According to one particular characteristic of the invention, a female jaw possesses an inside machining with slanted sides closing towards the bottom which contains two jaw extremities of the corresponding profile. Each jaw extremity is mainly composed of a vertical leg surmounting a ribbed support plate, said leg having one external wall being slanted by an angle corresponding to the slope of the slanted sides of the female clamping jaw. Two arc shaped shoulders on each side of the support plate form a protuberance with respect to said plate.

According to another characteristic of the invention, a male clamping jaw contains a knurled nut acting by means of a threaded rod on a control core for driving in the jaw extremities inside the female clamping jaw.

Moreover, inside the control core, a knurled nut acts on one flanging corner localized between the jaw extremities to apply said flanging corner on the top of the test piece for the compression tests.

BRIEF DESCRIPTION OF THE DRAWINGS

Other particular characteristics of the invention shall appear more readily from a reading of the following description of embodiments, given by way of non-restrictive examples, with reference to the accompanying drawings on which.

DETAILED DESCRIPTION OF THE PREFERRED EMBODIMENT

Figure 1:
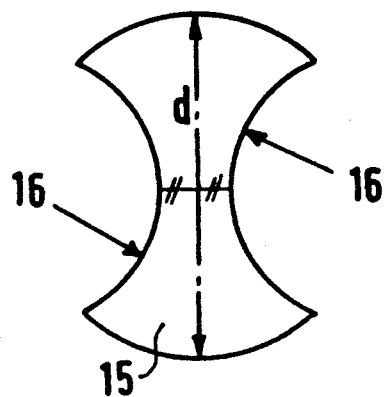
FIGS. 1 and 2 are front and profile views of a test piece.
Figure 2:
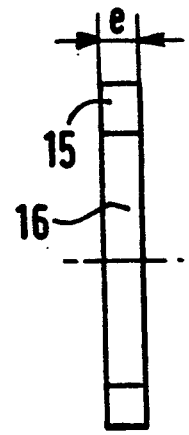

FIGS. 1 and 2 show a pellet-shaped test piece 15 with a relatively small thickness (between 3 and 5 mm, for example) with respect to the diameter (about 25 mm, for example), two half-moon shaped notches 16 being symetrically embodied in said pellet at one diameter, said notches having a relatively large diameter (20 mm, for example). Thus, the traction of the test piece is significantly reduced to a suitable value for the conducting of mechanical tests, but also to facilitate sampling of the test piece for a traction test. The test in question may possibly be protected against oxidation and shall have undergone an atmospheric re-entry simulation.

Figure 3:
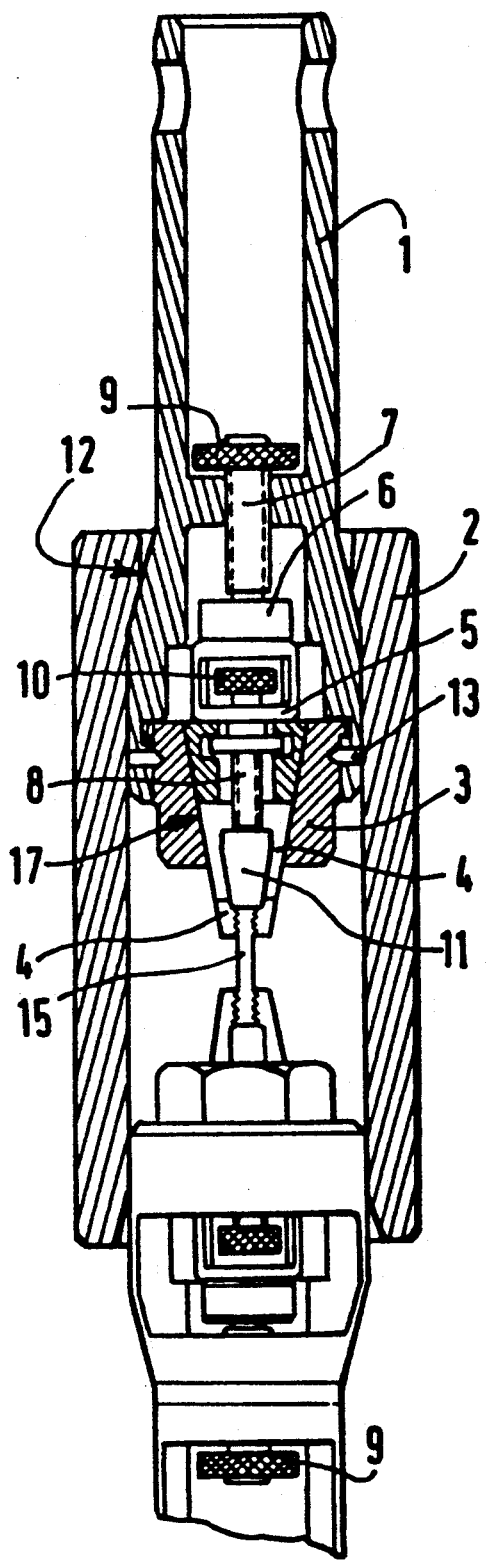
FIG. 3 is a cutaway view of test tooling equipment.

FIG. 3 shows a traction tool used to provide this type of test. It is constituted by a male support jaw 1 cooperating with a guiding sleeve 2 by means of its slanted walls 12. A female jaw 3 is fixed inside the extremity of the jaw 1 by locking screws 13. This generally tubular-shaped female jaw 3 has an inside machining with slanted sides 17 closing towards the bottom which contains two jaw extremities 4, also with a corresponding profile in support on the female jaw. A knurled nut 9 inside the male jaw 1 makes it possible to move a threaded rod 7 in support on a bolt 6 integral with a control core 5. Another knurled nut 10 inside the core is able to act on another threaded rod 8 whose lower extremity abuts against a flanging corner 11 localized inside the female jaw between the jaw extremities 4. The extremity profile of the flanging corner is rounded so as to be applied precisely on the rounded edge of the test piece.

The sleeve 2 contains at its lower portion another identical male jaw 2. The jaw extremities 4 of each jaw stretch the test piece 15 subjected to the traction tests.

Figure 4:
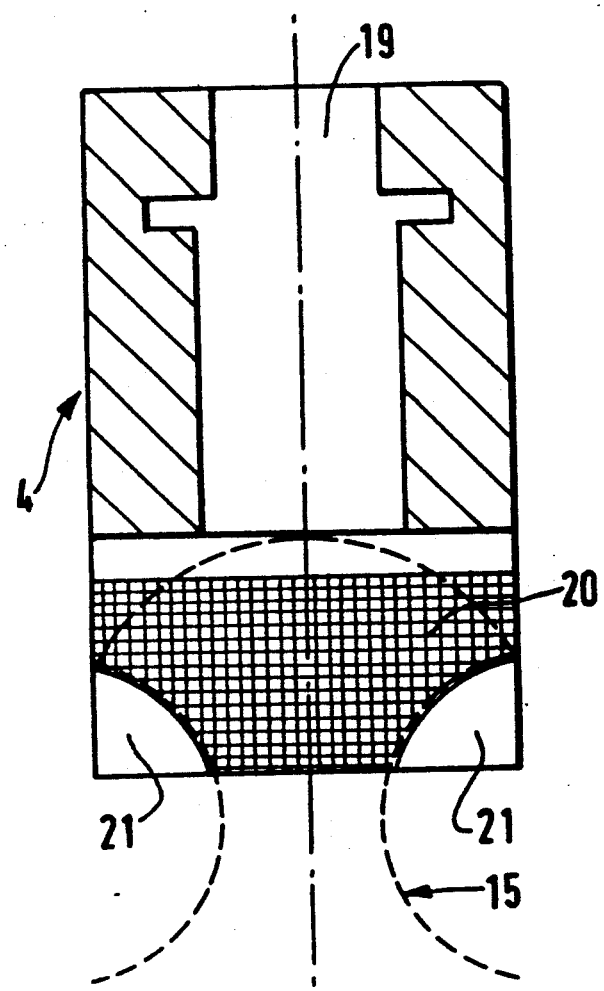
FIGS. 4 and 5 are front and profile views of a jaw extremity.
Figure 5:
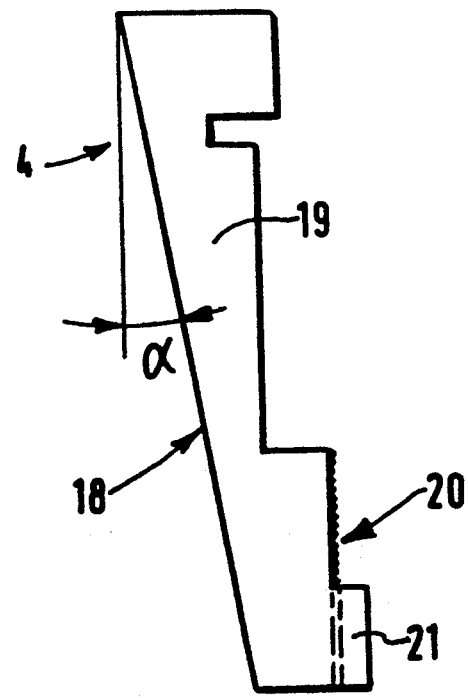
Figure 6:
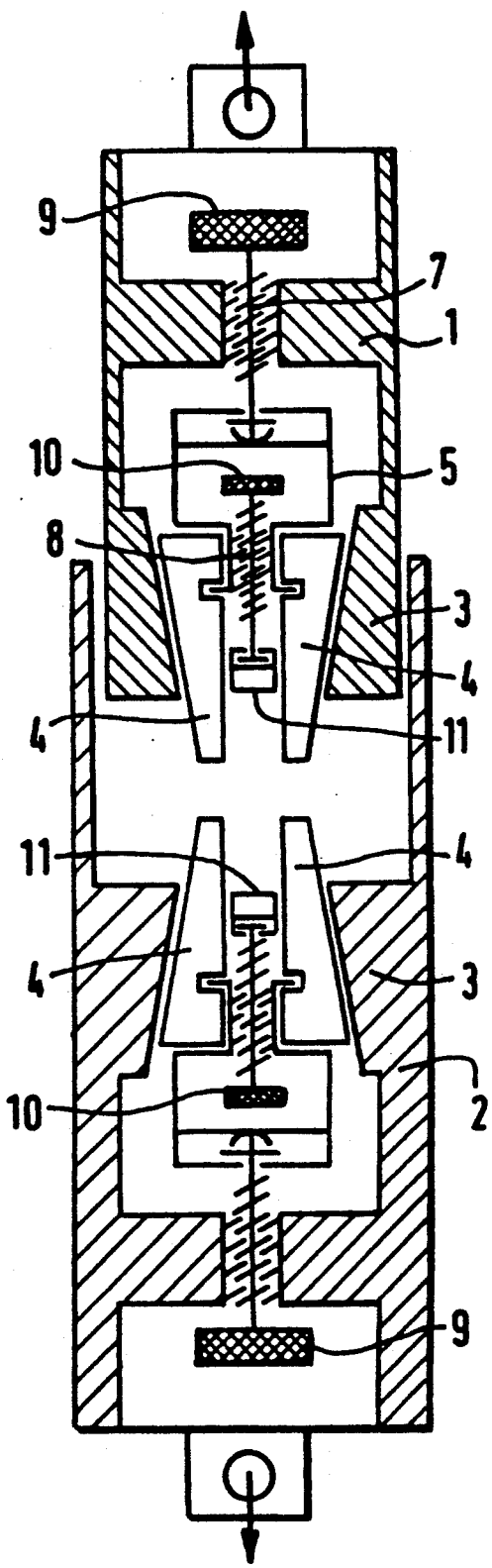
FIG. 6 is a simplified diagrammatic representation of the tooling equipment of FIG. 3, FIGS. 7 and 8 are diagrammatic views of the traction and compression test tooling equipment.

Each jaw extremity 4 is shown in more detail on FIGS. 4 and 5. It is mainly composed on a vertical leg 19 surmounting a support plate 20, said leg having one external wall 18 being slanted by an angle $\alpha$ of about 10 degrees with respect to vertical corresponding to the slope of the slanted sides 17 of the female jaw. The support plate 20 at the lower portion of the jaw extremity 4 is ribbed, thus improving clamping with the test piece. On each side of this support plate 20, two arcs of circle-shaped shoulders 21 form a protuberance with respect to said ribbed plate. The arc of a circle has the same radius as that of the half-moon notches 16 provided on the test piece 15. By virtue of this particular disposition, the test piece is positioned in support on the two shoulders 21, as shown by the dots on FIG. 4. FIG. 6 is a simplified diagrammatic representation of the tooling equipment shown on FIG. 3. The female jaws 3 are diagrammatized by slanted slanted edges provided on the male jaw 1 and on the sleeve 2. This figure also shows the threaded rods 7 and 8 connecting the knurled nuts 9 and 10 and of course the jaw extremities 4 and flanging corners 11.

As the test piece is thus maintained between the jaw extremities 4 of each clamping jaw (FIG. 3), the knurled nuts 9 are actuated so as to move the rod 7 in the direction of a compression of the core 5 and to drive in the jaw extremities 4 inside the female clamping jaw 3 expressed by an accentuation of clamping of the ribbed surfaces 20 on the test piece by virtue of the slope of the wall 18. Once the test piece is clamped, a traction test is carried out.

Figure 7:
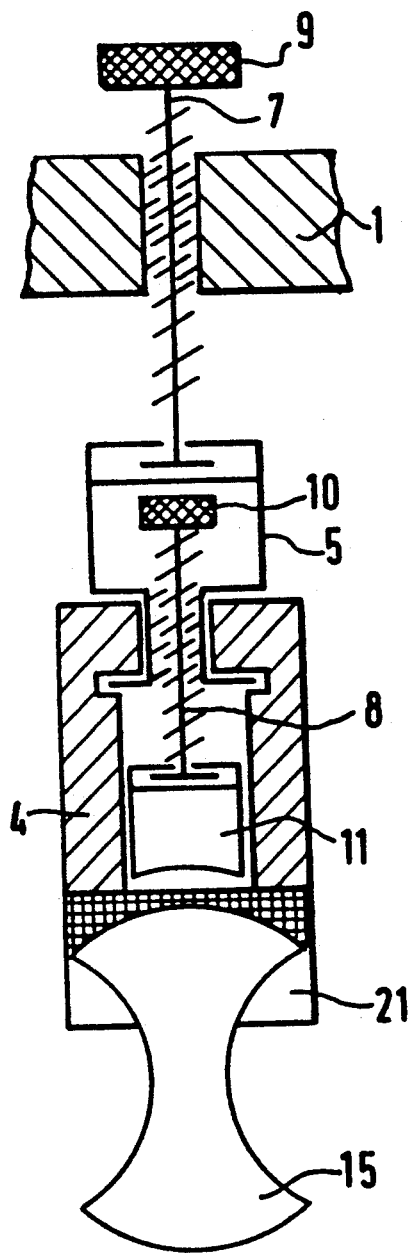

In order to do this, the two male clamping jaws are pulled in opposing directions. As the test piece abuts against the shoulders 21 of the jaw extremities 4, said test piece is adjusted on each side of the latter on the two machined arcs of a circle. The traction action on the clamping jaw 1 accentuates the clamping action of the jaw extremities 4 in the female clamping jaw 3 owing to the slope of their wall 18. This lateral self-closing clamping, which amplifies with the load, makes it possible to support the test peice during the test, the ribbed surface 20 avoiding any shifting of the piece clamped between the jaw extremities and the test piece. FIG. 7 diagrammatically shows what occurs during this traction test. In this case, the relative position of the threaded rod 7 and the rod 5 with respect to the male clamping jaw 1 remains unchanged. On the other hand, the threaded rod 8 and its knurled nut 10 able to move freely inside the core 5 ascend inside the female clamping jaw. The flanging corner 11 is then distanced from the test piece.

Figure 8:
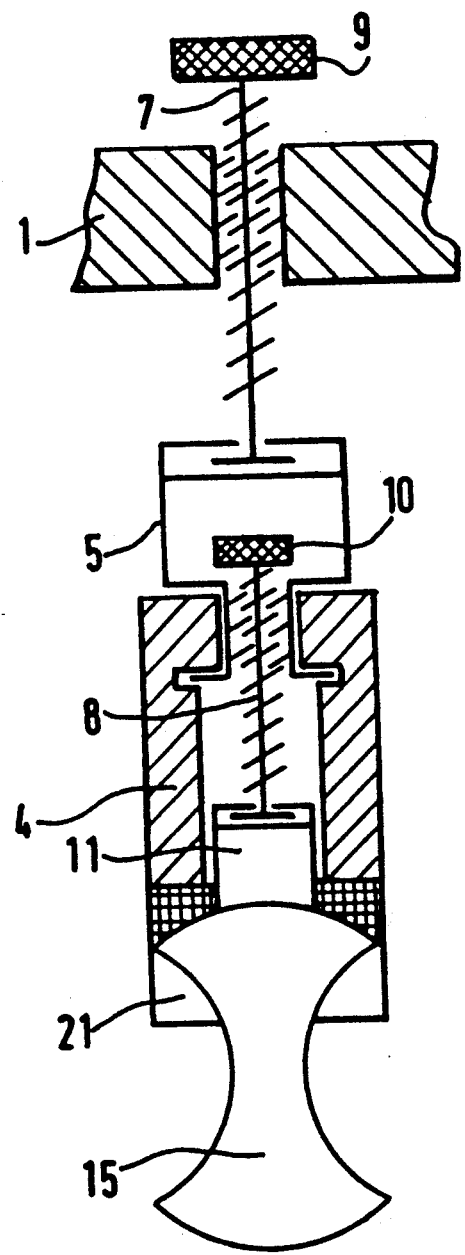

When a compression test is desired to be carried out, as shown on FIG. 8, the knurled nut 10 is actuated so as, with the aid of the threaded rod 8, to apply the flanging corner 11 on the top of the test piece. By acting in the opposite direction, the test piece is compressed with the aid of the opposing flanging corners.

Thus, the same tooling able to be adjusted with the arcs of a circle of the extremities of the test piece may be used for both traction and compression tests without the risk of ruptures starting owing to shearing via contacts with the tooling during the traction tests.

The tests thus conducted make it possible to use additional information for quantifying the residual traction or compression resistance of a material following an atmospheric re-entry.

What is claimed is:

1. A device for the traction and compression testing of a test piece following an atmospheric re-entry, the test piece having a shape corresponding to a pellet in which two arc-shaped notches have been formed, the device comprising tooling equipment connected to self-closing traction clamping jaws by self-closing means, said tooling equipment being able to abut arcs of the extremities of the test piece and being able to be used for both the traction and compression tests.

2. A device according to claim 1, wherein a female clamping jaw possesses an inside machining with slanted sides, said clamping jaw containing two jaw extremities of corresponding profile.

3. A device according to claim 2, wherein each jaw extremity is mainly composed of a vertical leg surmounting a ribbed support plate, one external wall of said leg being slanted by an angle $\alpha$ corresponding to the slope of the slanted sides of said female clamping jaw.

4. A device according to claim 3, wherein on each side of the support plate, two arc shaped shoulders form a protuberance with respect to said plate.

5. A device according to claim 2, wherein a male clamping jaw contains a knurled nut acting by means of a threaded rod on a control core for driving in the jaw extremities inside the female clamping jaw.

6. A device according to claim 5, wherein inside the control core, a knurled nut acts on a flanging corner located between the jaw extremities so as to apply said flanging corner on the top of the test piece.

7. A device according to claim 6, wherein the extremity profile of the flanging corner is rounded so as to be applied precisely to a rounded top of the test piece.

8. A device according to claim 2, wherein each jaw extremity has a support plate and on each side of each said support plate, two arc-shaped shoulders form a protuberance with respect to said plate.

9. A device according to claim 1, wherein a male clamping jaw contains a knurled nut acting by means of a threaded rod on a control core for driving in the jaw extremities inside a female clamping jaw.

* * * * *